US010485693B2

(12) United States Patent
Matsuura

(10) Patent No.: US 10,485,693 B2
(45) Date of Patent: Nov. 26, 2019

(54) EJACULATION PROMOTION APPARATUS AND EJACULATION PROMOTION DEVICE

(71) Applicant: TENGA Co., Ltd., Minato-ku, Tokyo (JP)

(72) Inventor: Tsutomu Matsuura, Tokyo (JP)

(73) Assignee: TENGA Co., Ltd., Minato-ku, Tokyo (JP)

( * ) Notice: Subject to any disclaimer, the term of this patent is extended or adjusted under 35 U.S.C. 154(b) by 253 days.

(21) Appl. No.: 15/518,482

(22) PCT Filed: Oct. 27, 2014

(86) PCT No.: PCT/JP2014/078466
§ 371 (c)(1),
(2) Date: Apr. 11, 2017

(87) PCT Pub. No.: WO2016/067333
PCT Pub. Date: May 6, 2016

(65) Prior Publication Data
US 2017/0231801 A1 Aug. 17, 2017

(51) Int. Cl.
*A61H 19/00* (2006.01)
*A61B 10/00* (2006.01)
*A61F 5/41* (2006.01)

(52) U.S. Cl.
CPC ............ *A61F 5/41* (2013.01); *A61B 10/0058* (2013.01); *A61H 19/00* (2013.01); *A61H 19/32* (2013.01)

(58) Field of Classification Search
CPC ........ A61H 19/00; A61H 19/30; A61H 19/32; A61B 10/0058
See application file for complete search history.

(56) References Cited

U.S. PATENT DOCUMENTS

| 5,807,360 A | 9/1998 | Shubin |
| D674,907 S | 1/2013 | Matsuura |
| (Continued) |

FOREIGN PATENT DOCUMENTS

| DE | 20 2011 005 508 U1 | 9/2011 |
| JP | H05-000126 U | 1/1993 |
| (Continued) |

OTHER PUBLICATIONS

International Search Authority/JPO, International Search Report dated Jan. 27, 2015 in International Patent Application No. PCT/JP2014/078466 (with English translation), 4 pages.
(Continued)

*Primary Examiner* — Thaddeus B Cox
(74) *Attorney, Agent, or Firm* — Masuvalley & Partners

(57) ABSTRACT

Provided are an ejaculation promotion apparatus and an ejaculation promotion device by which a varied stimulus and tightening force by an appropriate pressure can be obtained, by using an air pressure in a non-closed air cell formed between a core member and a container as a pressure source that provides a stimulus and tightening force to a penis. Included are a core main body (31) including an insertion inlet (33) and an insertion empty space (35), a plurality of first ribs (40) projectingly provided on an outer peripheral surface of the core main body at necessary intervals, and extending in an approximately the same direction, and an air resistance member (50) that allows passage of air along a flow path F while serving as a resistance against the air flowing in the flow path at the time of expansion of an outer diameter of the core main body.

6 Claims, 9 Drawing Sheets

(56) References Cited

U.S. PATENT DOCUMENTS

| | | |
|---|---|---|
| 2007/0179336 A1 | 8/2007 | Knyrim |
| 2008/0004577 A1 | 1/2008 | Matsuura |
| 2010/0130897 A1 | 5/2010 | Knyrim |

FOREIGN PATENT DOCUMENTS

| | | |
|---|---|---|
| JP | H10-99361 A | 4/1998 |
| JP | 2007-526047 A | 9/2007 |
| JP | 3135794 U | 9/2007 |
| JP | 2010-125323 A | 6/2010 |
| JP | 4878346 B2 | 2/2012 |
| WO | 2006/132125 A1 | 12/2006 |

OTHER PUBLICATIONS

International Search Authority/JPO, Written Opinion dated Jan. 27, 2015 in International Patent Application No. PCT/JP2014/078466, English Translation 5 pages.

EPO, The Extended European Search Report dated Oct. 20, 2017 in EP Patent Application No. 14904837.3 (PCT/JP2014/078466), 8 pages.

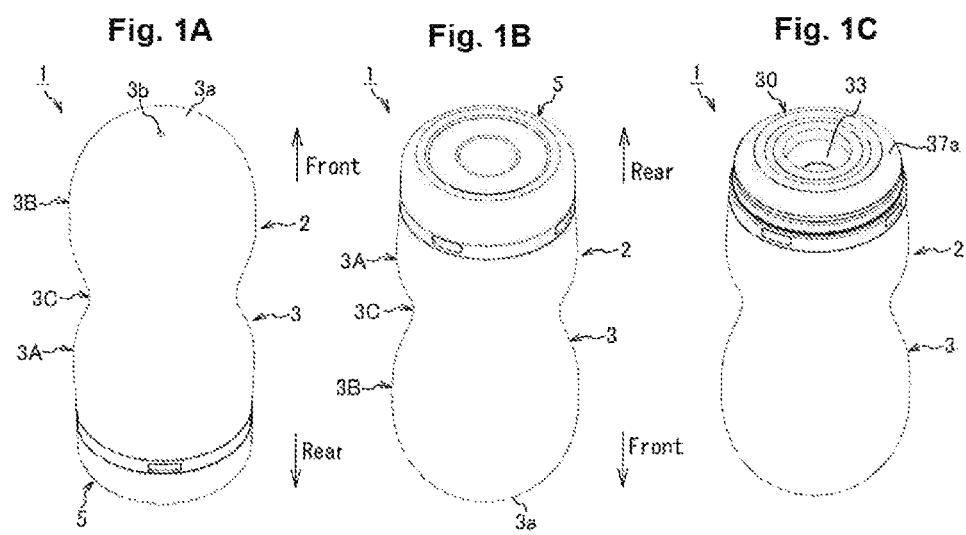

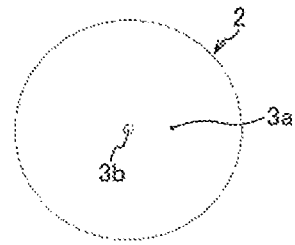
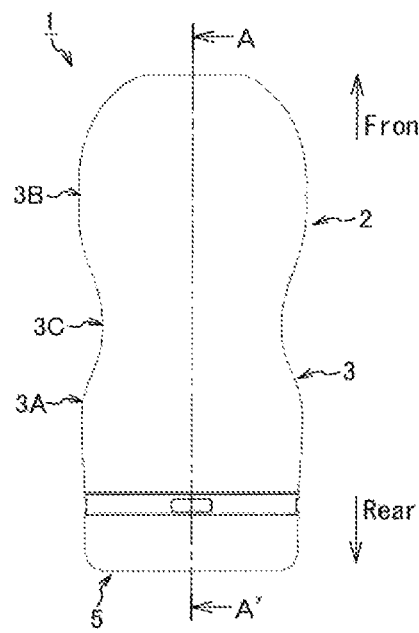
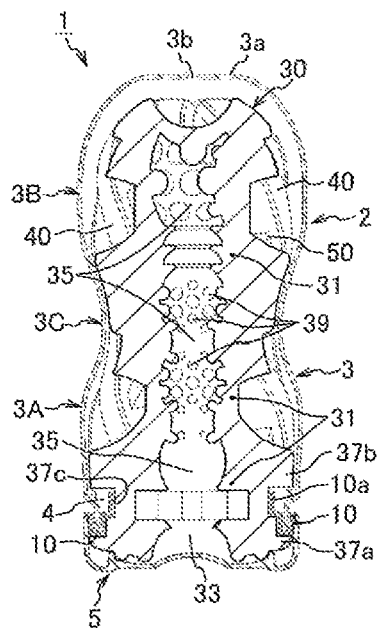
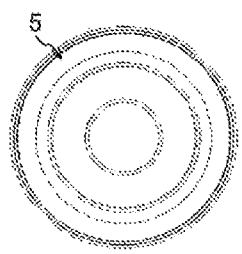

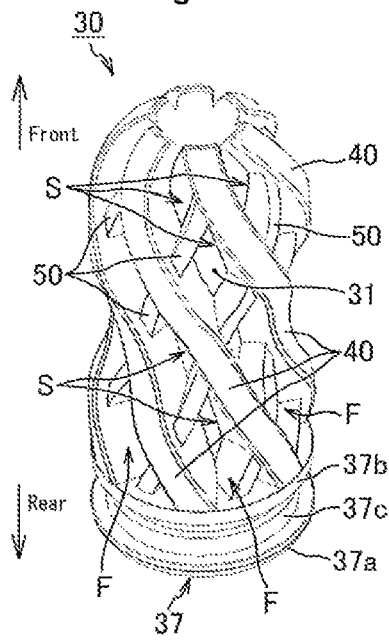 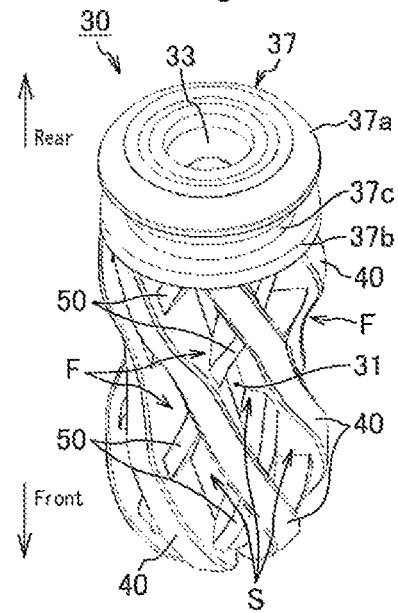

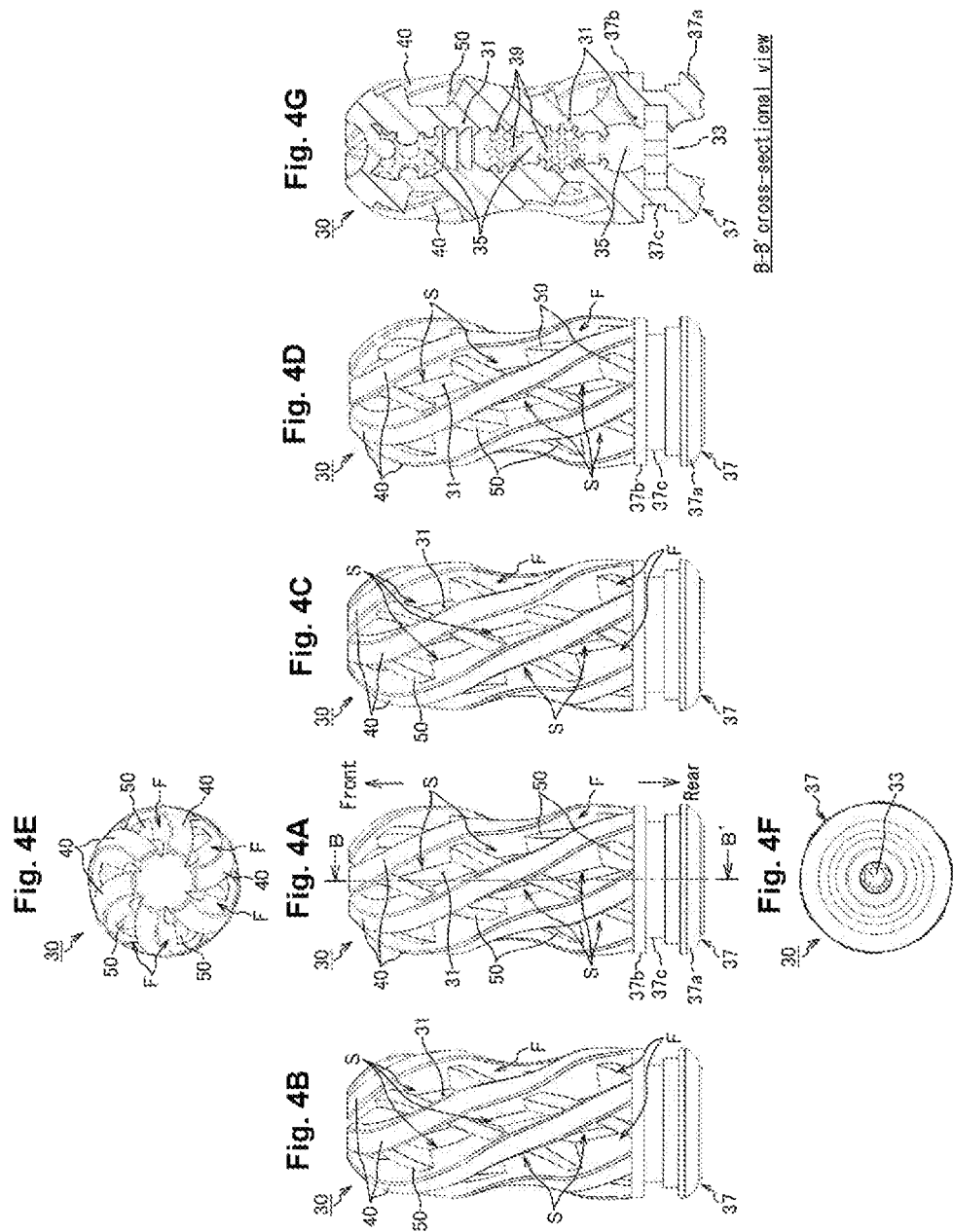

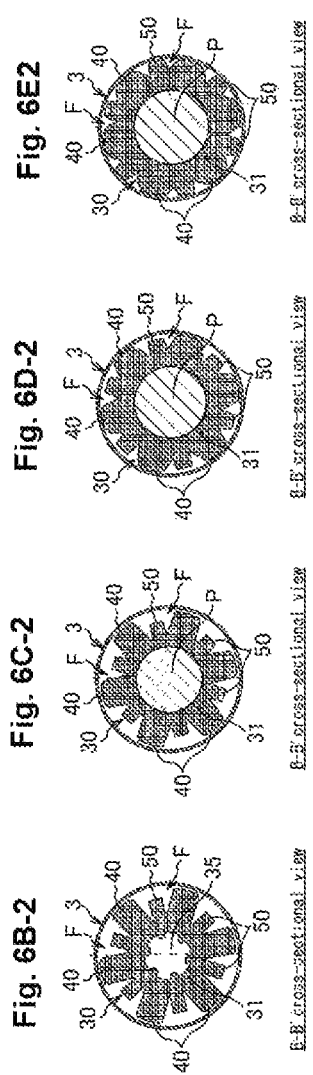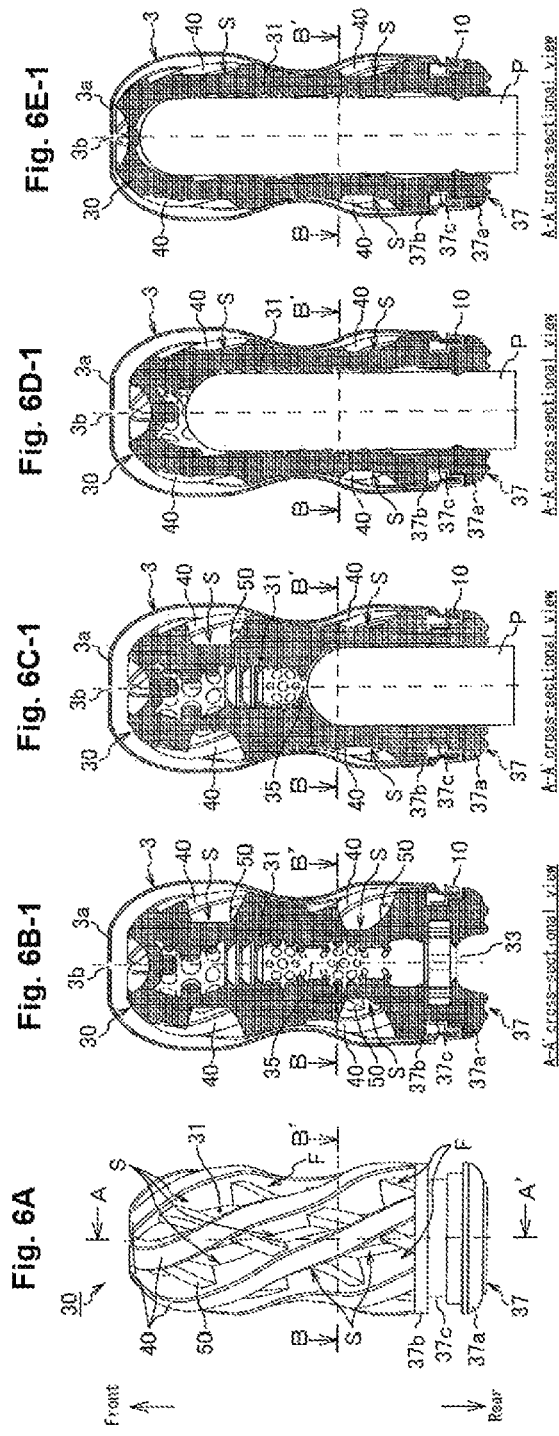

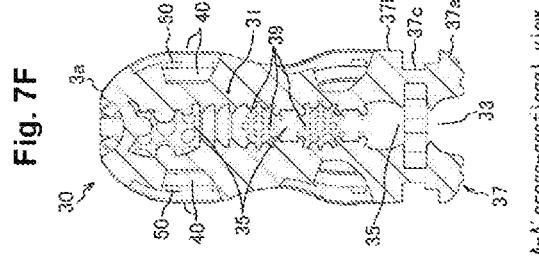
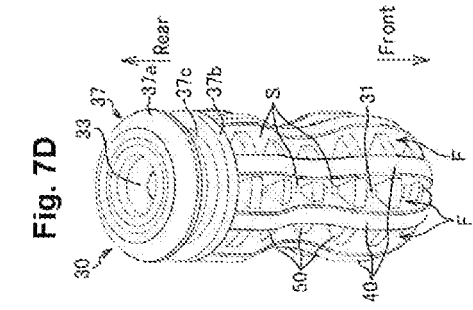
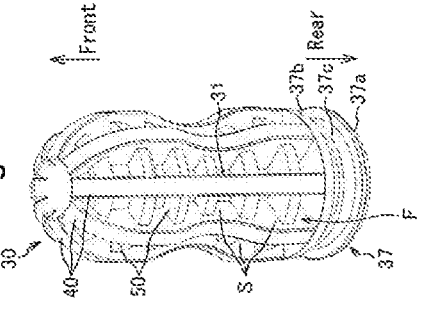
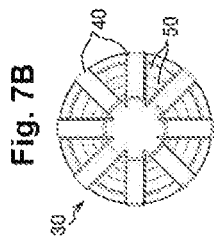
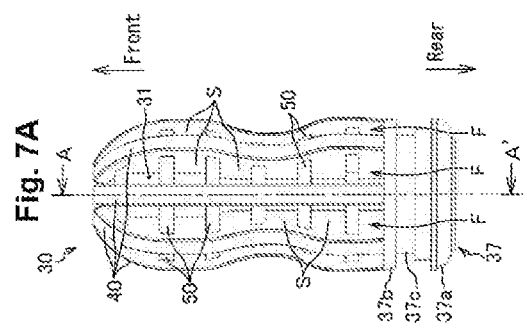
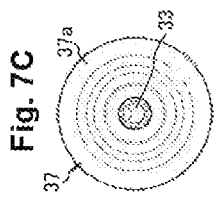

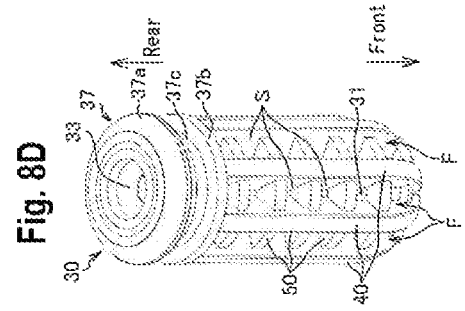
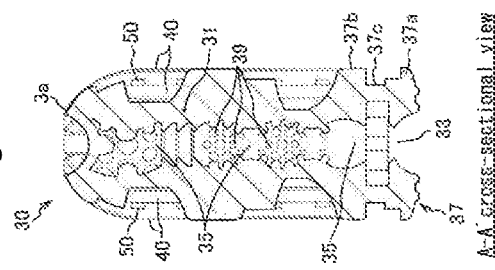
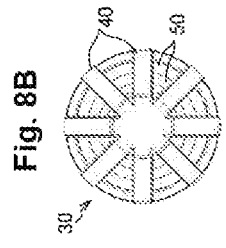
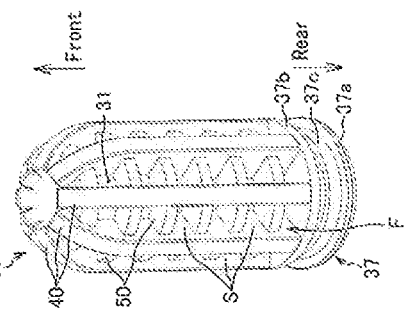
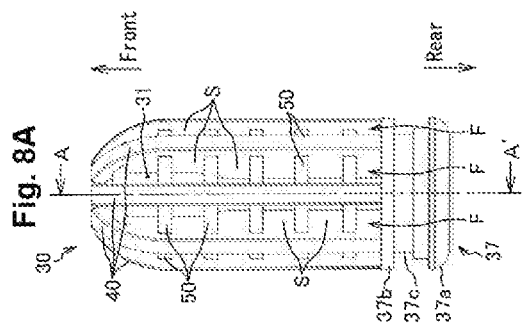
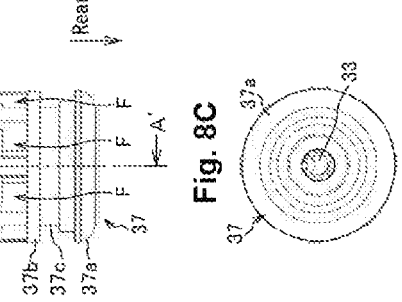

US 10,485,693 B2

EJACULATION PROMOTION APPARATUS AND EJACULATION PROMOTION DEVICE

RELATED APPLICATIONS

This application is the U.S. National Phase of and claims priority to International Patent Application No. PCT/JP2014/078466, International Filing Date Oct. 27, 2014; which is incorporated herein by reference in its entirety.

TECHNICAL FIELD

The present invention relates to an ejaculation promotion apparatus and an ejaculation promotion device, and especially relates to improvement of an ejaculation promotion apparatus and an ejaculation promotion device that have been conventionally used based on demands for medical study and treatment, and social demands such as avoidance of sexual crimes, prostitution, and a spread of sexually transmitted diseases.

BACKGROUND ART

Various ejaculation promotion devices (sperm collection devices) for collecting sperms of males have been proposed for needs of medical study and treatment. For example, the ejaculation promotion devices are used for medical needs such as an examination of a sexual function of the husband from sperms collected to determine the cause of infertility of a couple, treatment of sexual functional disorder, and securing and storing the sperms for artificial insemination. Further, to meet various social needs such as prevention of sexual crimes by fulfilling personal sexual needs, avoidance of prostitution and a decrease in the number of sexual disease infected patients, simplified ejaculation promotion devices which are inexpensive and do not raise hygiene and health problems because they are disposable or washable have been known.

For example, Patent Document 1 (JP 4878346 B1 (WO 2006/132125 A1)) discloses an ejaculation promotion device composed of a cylindrical container body with one end in a longitudinal direction open, and a core member made of a gel-like resin accommodated in the container body and including an insertion empty space extending from an insertion inlet in the one end in the longitudinal direction to an inside.

The ejaculation promotion device forms a plurality of sealed empty spaces among an outer surface of a core main body, a plurality of ribs, and an inner wall of a container body, by projectingly providing the plurality of ribs on an outer peripheral surface of the core main body that configures a core member in a mesh manner, pressurizes a penis inside the core main body by an air cushion function brought by these sealed empty spaces, and enhances a stimulus.

However, in this ejaculation promotion device, the plurality of completely airtight sealed spaces is formed between the inner wall of the container body and the outer surface of the core main body at the time of press-fitting the penis into the insertion empty space of the core main body and expanding the core member, and thus a pressure applied to the penis from the inner wall of the insertion empty space is more likely to be excessive. Therefore, the pressure becomes a resistance against a free action of the penis, and problems such as difficulty in smoothly moving (rubbing) the penis back and forth in the insertion empty space and a difficulty in providing an effective stimulus by the rubbing to a front end section (glans) of the penis have been pointed out.

Further, in a case where an old man, a physically handicapped person, or the like, who is more sensitive to the stimulus than a healthy young man, uses this type of collecting device, the person receives a strong stimulus that is not suitable for the person, due to excessive air pressure force applied to the penis from the sealed spaces, and the objectives of ejaculation promotion and sperm sampling may not be able to be achieved.

Further, if the penis is continuously forcefully rubbed against an inner pressure generated due to the sealed spaces, there is a problem that air in the insertion empty space that has no way out is removed between the insertion inlet of the insertion empty space and the penis, and the inside of the insertion empty space is moved into a nearly vacuum state. If the air comes out of the insertion empty space and the insertion empty space becomes in a vacuum state, the inner wall of the insertion empty space overly adheres (sticks) to an outer surface of the penis, and rubbing becomes impossible. Therefore, it becomes necessary to pull out the penis of the insertion empty space once, and insert the penis again. Even if a lubricant is filled in the insertion empty space, this defect occurs. Such an operation that requires frequent do-overs of insertion provides dissatisfaction to users, and becomes a cause to decrease the product value such as a loss of a willingness to ejaculate.

Further, the gel-like resin that is a material configuring the core member is expensive, and thus it is clear that reduction of a use amount contributes to cost reduction. However, if the ribs are provided in an intersecting state with the outer surface of the core main body in a mesh manner, the use amount of the gel-like resin is increased in proportion to the number of ribs, and becomes a cause to hinder the reduction of manufacturing cost.

In a semen collecting device disclosed in Patent Document 2 (JP Hei 10-99361A (U.S. Pat. No. 5,807,360)), a plurality of ribs extending in an axial direction is provided in parallel on an outer surface of a gel-like insertion body. When a penis is inserted into the insertion body and the insertion body expands, a plurality of long spaces extending in the axial direction is formed between the ribs and an inner wall of a container. However, these spaces are open at a front end section of the insertion body, and it is clear that these spaces are non-sealed spaces. Further, no obstacles that hinder movement of air exist in the non-sealed spaces. Therefore, an air flow generated in the non-sealed spaces by insertion of the penis promptly flows along a longitudinal direction of the insertion body.

When the penis is inserted into the insertion body and rubbing is performed in a state where such an insertion body is accommodated in the container, the air in the long and narrow spaces is depressed by a front end section of the penis, and promptly moves further to a front end side prior to the front end section of the penis. Therefore, the air in a portion of a space corresponding to an outer periphery of the front end section of the penis is in a state of being pushed forward on a steady basis, and the air is not stagnated in this space portion (a sufficient pressure is not applied to the front end section of the penis). Therefore, it is clear that providing a stimulus by air cushion (air pressure) to the front end section of the penis is difficult.

Further, in the semen collecting device of Patent Document 2, a hole is opened in the front end section of the gel-like insertion body. Therefore, the semen ejected into the insertion body is discharged through the hole into the container, and the outer surface of the insertion body and the container are stained and washing is burdensome.

SUMMARY OF THE INVENTION

The present invention has been made in view of the foregoing, and an objective is to provide an ejaculation promotion apparatus and an ejaculation promotion device by which a varied stimulus and tightening force by an appropriate pressure can be obtained, by using an air pressure (an adjustable air pressure by air removal) in non-closed air cells (non-airtight dead air spaces) formed between the core member and the container as a pressure source that provides a stimulus and tightening force to a penis.

That is, by use of an air pressure adjustment capacity using the non-closed air cells, which cannot be obtained with the sealed spaces that cannot perform air removal, that is, by use of a proper air pressure, the pressure adjustment and change can be arbitrarily performed according to the user's preference without making pressurizing force to the penis excessive.

That is, elimination of defects such as an excessive stimulus to the penis, which is a defect caused when a plurality of sealed spaces is formed between the core member and the container, out of use due to leakage of the air in the core member, and do-overs of the insertion operation is intended.

Further, effective achievement of cost reduction by decreasing use materials of air resistance members, of first ribs and the air resistance members (second ribs) that form the non-closed air cells is intended.

Further, the use material of the air resistance member is decreased compared with the first ribs, and thus the volume of the entire core member is decreased and work of taking in and out the core member to/of the container becomes easy. Therefore, washing the core member after use, attaching the core member into the container again and re-using the device can be repeated, which is cost efficient.

In order to achieve the above object, an ejaculation promotion apparatus according to the present invention is an ejaculation promotion apparatus made of a gel-like resin, accommodated in a container body with at least one end surface in an axial direction open, including an insertion empty space extending from an insertion inlet in the one end surface in the axial direction into an inside, and having a core main body including the insertion inlet and the insertion empty space, and a plurality of first ribs projectingly provided on an outer peripheral surface of the core main body at necessary intervals and extending in approximately parallel to one another. And, each of the first rib comes in contact with an inner wall of the container body to forma flow path extending in the axial direction or a direction inclined with respect to the axial direction with the adjacent first rib at least at a time of expansion of the core main body, and an air resistance member that allows passage of air along the flow path while serving as a resistance against movement of the air is provided in the flow path at a time of expansion of an outer diameter of the core main body.

An ejaculation promotion device according to the present invention comprises the ejaculation promotion apparatus according to the above, and a container body accommodating the ejaculation promotion apparatus in an opening in one end surface in an axial direction.

According to the present invention, a cause to impede an objective of ejaculation by generating excessive air pressure force between the expanded core main body and the inner wall of the container body when the penis is inserted into the core main body and applying an excessive pressure to the penis, or a defect of leakage of the air between the penis and the insertion inlet of the insertion empty space due to an excessive increase in the inner pressure of the core main body can be eliminated.

BRIEF DESCRIPTION OF THE DRAWINGS

FIGS. 1A, 1B, and 1C are an external perspective view of an ejaculation promotion device according to an embodiment of the present invention from a front end side, an external perspective view from a rear end side, and an external perspective view illustrating a container body and a core member in a state where a cap is removed.

FIGS. 2A, 2B, 2C, and 2D are a front view, a top view, a bottom view, and an A-A' cross-sectional view of the ejaculation promotion device.

FIGS. 3A and 3B are a front end-side perspective view and a rear end-side perspective view of the core member (ejaculation promotion apparatus) according to the embodiment.

FIGS. 4A to 4G are a front view, a left view, a right view, a rear view, a top view, a bottom view, and a B-B' cross-sectional view of the core member.

FIG. 6A is a front view of the core member (ejaculation promotion apparatus), FIGS. 6B-1 and 6B-2 are an A-A' cross-sectional view and a B-B' cross-sectional view illustrating a state in which an insertion object is not inserted in an insertion empty space, FIGS. 6C-1 and 6C-2 are an A-A' cross-sectional view and a B-B' cross-sectional view illustrating a state in which the insertion object is inserted into an intermediate portion in the insertion empty space, FIGS. 6D-1 and 6D-2 are an A-A' cross-sectional view and a B-B' cross-sectional view illustrating a state in which the insertion object is inserted in a deep portion of the insertion empty space, and FIGS. 6E-1 and 6E-2 are an A-A' cross-sectional view and a B-B' cross-sectional view illustrating a state in which the insertion object is inserted in the deepest portion of the insertion empty space.

FIGS. 7A to 7F are main configuration explanatory views of an ejaculation promotion apparatus according to a second embodiment of the present invention, and FIG. 7A is a front view, FIG. 7B is a top view, FIG. 7C is a bottom view, FIGS. 7D and 7E are perspective views, and FIG. 7F is an A-A' cross-sectional view.

FIGS. 8A to 8F are main configuration explanatory views of an ejaculation promotion apparatus according to a deformation example of the second embodiment of the present invention, and FIG. 8A is a front view, FIG. 8B is a top view, FIG. 8C is a bottom view, FIGS. 8($d$) and 8($e$) are perspective views, and FIG. 8F is an A-A' cross-sectional view.

DETAILED DESCRIPTION OF PREFERRED EMBODIMENT

First Embodiment (Basic Configuration)

Figure 5A:
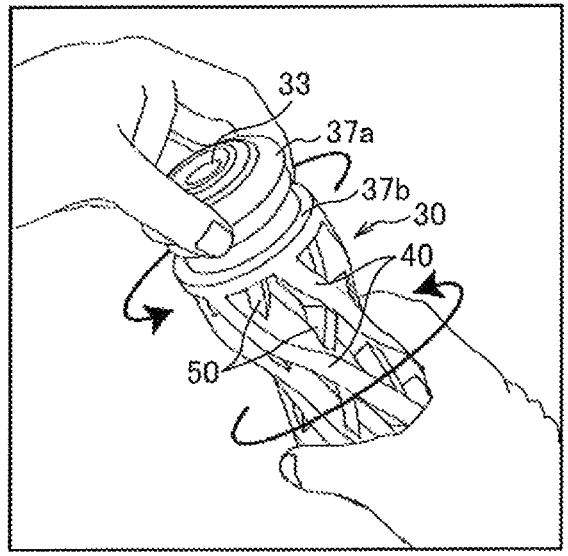
FIGS. 5A and 5B are explanatory views illustrating a procedure of inserting the core member into the container body while twisting the core member.

Hereinafter, the present invention will be described in detail according to an illustrated embodiment.

FIGS. 1A, 1B, and 1C are external perspective views of an ejaculation promotion device according to an embodiment of the present invention. FIG. 1A is an external perspective view from a front end side, FIG. 1B is an external perspective view from a rear end side and FIG. 1C is external perspective view illustrating a container body and a core member in a state where a cap is removed. FIGS. 2A, 2B, 2C, and 2D are a front view, a top view, a bottom view, and an A-A' cross-sectional view of the ejaculation promotion device. FIGS. 3A and 3B are a front end-side perspective view and a rear end-side perspective view of the core member (ejaculation promotion apparatus) according to the embodiment.

FIGS. 4A to 4G are a front view, a left view, a right view, a rear view, a top view, a bottom view, and a B-B' cross-sectional view of the core member.

An ejaculation promotion device (sperm collection device) 1 includes a container 2 composed of a cylindrical container body 3 having one end surface in a longitudinal direction (axial direction) open and including a small-diameter portion 3C in an appropriate place (intermediate portion) on an outer peripheral surface and a cap 5 attached or removed to/from an opening 4 of the container body 3 and opens/closes the opening 4, and a core member (ejaculation promotion apparatus) 30 made of a gel-like resin accommodated in the container body 3, and including an insertion empty space 35 extending from an insertion inlet 33 in the one end surface in the longitudinal direction (axial direction) into an inside.

The container body 3 is configured from a resin material having a necessary thickness, and is a non-cylindrical body where an outer diameter of the intermediate portion (small-diameter portion) 3C is smaller than outer diameters of both end sections (large-diameter portions 3A and 3B) in the longitudinal direction. The shape of a connected portion of the large-diameter portion 3A and the intermediate portion 3C, and a contour shape of a connected portion of the large-diameter portion 3B and the intermediate portion 3C are arc shapes (curved shapes).

An air removal small hole (air removal hole) 3b is formed in the other end section 3a of the container body 3 as needed, and is sealed with a seal (not illustrated) at the time of non-use. At the time of use, the seal is removed, and the small hole 3b is closed and opened with a finger, so that the degree of adhesion or feeling of adhesion (feeling of absorption or feeling of sucking) between an inner wall of the core member and a penis can be adjusted. That is, tightening force becomes large because the penis adheres to the inner wall of the core member in a state where the small hole 3b is blocked, and the tightening force becomes small in a state where the small hole is opened. As described above, the tightening force (a pressure difference from the atmospheric pressure) is changed by a simple operation of only opening/closing the small hole, and a stimulus can be changed. In a case where a pain is felt in the penis, the small hole may just be opened.

In more details, when the penis is inserted into the insertion empty space 35 through the insertion inlet 33 in the state where the small hole 3b is opened, the core member can maintain original flexibility (deformable), and thus the penis can smoothly move back and forth in the insertion empty space.

Meanwhile, when the penis is inserted in the insertion empty space 35 in the state where the small hole is opened, and then the small hole 3b is blocked and the penis moves toward the insertion inlet 33 side, a phenomenon called vacuum occurs, where an inner wall of the insertion empty space is stuck to an outer surface of the penis. In the vacuum state, the penis is stuck to the inner wall of the insertion empty space, and thus the penis less smoothly moves back and forth in the insertion empty space. However, feeling of sticking can be obtained.

The core member (ejaculation promotion apparatus) 30 is an approximately bag-like body configured from a gel-like resin having viscosity such as elastomer or gel-like rubber. The core member 30 includes a large-diameter flange (annular rib) 37 in an insertion-side end surface, and the insertion empty space 35 having a larger diameter than the insertion inlet is formed in communication with an inside of the small-diameter insertion inlet 33. Projections, or folds or the like 39 are formed in the insertion empty space 35 in an arbitrary arrangement. An appropriate amount of lotion or the like as a lubricating liquid is filled in the insertion empty space 35.

As illustrated in FIG. 2(d), the flange 37 of the core member includes a first flange 37a positioned at a rear end, a second flange 37b positioned close to a front end, and a concave portion 37c positioned between the both flanges.

An inner diameter-side convex portion 10a of a ring-like locking member 10 locked with an opening end edge of the opening 4 is fitted into an concave portion 37c of the core member, so that the core member is fixed to the opening end edge of the container body. The concave portion 37c is formed in a stepwise manner, and the inner diameter-side convex portion 10a of the locking member 10 is also formed in a stepwise manner. Therefore, the stepwise portions are meshed with each other, so that the flange 37 of the core member is reliably locked with the locking member 10, and falling of the core member into the container body or dropout of the core member outside during use is prevented.

In a case where the small-diameter intermediate portion 3C is provided in the container body, the core member is fixed to the container body side by a pressure between the penis in the core member and the narrow portion, and thus pullout of the core member through the opening of the container body can be reliably prevented.

Since the concave portion 37c of the flange and the locking member 10 are not fixed, the core member can be attached or removed to/from the container body. Therefore, the core member taken out of the container body is washed alone and is then put back into the container body, and can be re-used in a clean state.

The core member (ejaculation promotion apparatus) 30 has a characteristic configuration as follows.

That is, the core member 30 includes a core main body 31 including the insertion inlet 33 and the insertion empty space 35, a plurality of first ribs 40 projectingly provided on an outer peripheral end edge of the core main body 31 at necessary intervals and extending in an approximately the same direction (nearly in parallel) to one another, and a plurality of second ribs (air resistance members) 50 projectingly provided on an outer peripheral surface (between the first ribs) of the core main body with necessary intervals and intersecting with the first ribs 40. The first ribs 40 and the second ribs 50 may intersect in a net-like manner in external view. However, the second ribs (air resistance members) that are projections that bring an air resistance in an appropriate place in a flow path may just be provided, and does not necessarily configure a net.

Further, at the time of expansion of an outer diameter of the core main body 31, each of the first ribs 40 comes in contact with an inner wall of the container body and forms a flow path F extending in an axial direction or in a direction inclined with respect to the axial direction with an adjacent first rib 40. The first rib 40 may have a linear shape in front view, or can be formed into an arbitrary shape in a curved manner, in a waveform manner, or in a zigzag manner.

The first rib may be in contact with the inner wall of the container body at the time of non-expansion of the core main body. Note that, to configure the core member to be freely taken in and out of the container, it is better to configure the first ribs to be easily separated from the inner wall of the container body at the time of non-expansion of the core main body.

Further, the second rib (air resistance member) 50 is configured to form a gap along the flow path F or an air-removable contact portion by deformation between an outer end edge (outer peripheral surface) of the second rib and the inner wall of the container body when the outer diameter of the core main body 31 expands and the first rib come in contact with the inner wall of the container (at the time of formation of the flow path F). In other words, the second rib 50 forms a non-closed air cell S with an adhering portion of the first rib, the outer peripheral surface of the core main body, another adjacent second rib, and the inner wall of the container body, when the first rib adheres to the inner wall of the container due to expansion of the core main body.

The second rib 50 is configured to allow passage of air along the flow path while serving as a resistance against the air flowing in the flow path F when the outer diameter of the core main body expands and an outer end edge of the first rib adheres to the inner wall of the container and forms the flow path. The present example has been configured to exhibit the above function by making a protruding length of the second rib (a protruding length from the outer peripheral surface of the core main body) shorter than a protruding length of the first rib 40. However, the second rib may be configured to have an easily elastically deformable shape, for example, in a thin manner, while having the same protruding length as the first rib. This is because the second rib can function as a safety valve that is elastically deformed and is separated from the inner wall of the container body when an ambient air pressure is increased, while serving as a resistance against the air flowing in the flow path, by being more easily elastically deformable than the first rib.

Note that the first rib sequentially forms the flow path F from the rear end side by being sequentially non-contact with the inner wall of the container as the core main body expands in a process of inserting the penis from the rear end side of the insertion empty space. Therefore, the non-closed air cell S is also sequentially formed from the rear end side, and the non-closed air cell is finally formed in the entire length of the flow path in the axial direction.

The first rib 40 extends from the rear end side (second flange 37b) of the core main body 31 up to the front end side, and a space between front end sections of the adjacent first ribs is opened. As illustrated in FIGS. 3(a) and 3(b) and FIGS. 4(a) to 4(g), an interval between the front end sections of the first ribs is substantially smaller than a width of a main body of the flow path.

Therefore, when the penis moves through the insertion inlet toward the inside of the insertion empty space, the air in the flow path F tries to flow from the rear end side to the front end side due to expansion of the core main body. However, smooth movement of the air is hindered by the second ribs 50 provided in the flow path at necessary intervals, and the air is temporarily stagnated in a front end section of the flow path where the width is considerably narrow (a moving speed is decreased).

That is, the core member 30 according to the present example includes the core main body 31 including the insertion inlet 33 and the insertion empty space 35, and the plurality of ribs 40 and 50 projectingly provided from the outer surface of the core main body 31 and intersecting with one another (in a net-like manner), and the outer end edges of the first ribs 40 come in contact with the inner wall of the container body 3 at the time of expansion of the core main body 31, whereby the flow paths F extending in an approximately axial direction are formed by the outer surface of the core main body, the plurality of first ribs 40, and the inner wall of the container body. The flow paths F are blocked by the first ribs in the state where the first ribs 40 adhere to the inner wall of the container body. That is, each of the flow paths F at the time of expansion of the core main body configures a space that hinders circulation of the air in a peripheral direction.

Note that it is favorable that each of the first ribs 40 adheres to the inner wall of the container body throughout the entire length at the time of expansion of the core main body throughout the entire length. However, it is not necessary to shield the flow paths F in an airtight manner in a strict sense. That is, it is not a problem that the flow paths F slightly communicate into each other through a concave portion, a hole, or a gap partially formed between an outer peripheral end edge of the first rib and the inner wall of the container body. That is, most of the air in the flow path F may just be moved along the individual flow path at the time of insertion of the penis or at the time of rubbing of the penis, and some leakage is permissible.

Figure 5B:
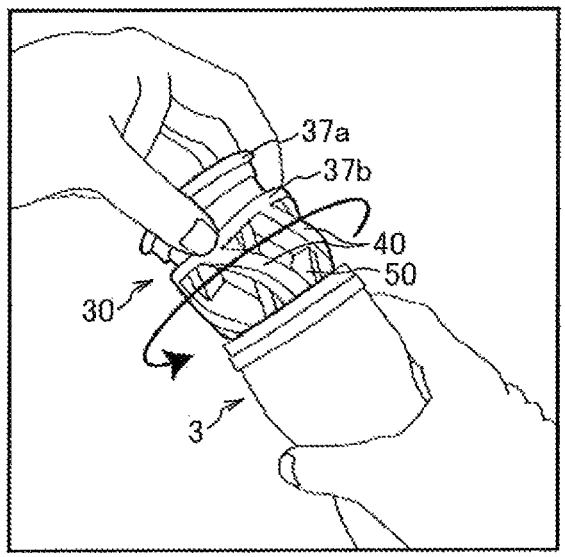

In the illustrated embodiment, the first rib 40 extends in the direction inclined with respect to the axial direction of the core main body in a spiral manner in the present example. An advantage of forming the first rib in a spiral manner is to compress and deform the core member in a spiral manner and easily insert the core member into the opening 4 of the container body by twisting the entire core member as illustrated in FIGS. 5A and 5B, in inserting the core member 30 into the container body 3. That is, in a case where the first rib extends straight in the axial direction, the first rib extending in the axial direction becomes a resistance and the core member cannot be easily twisted even if being tried to be twisted around its axial center. However, in a case where the first rib extends in a spiral manner (a direction diagonally intersecting with the axial direction), the entire core member can be easily deformed in the twisting direction, and thus can be twisted and a dimension in a radius direction can be compressed. Therefore, the core member can be easily inserted through the opening 4. In a case where the core member accommodated in the container body is taken out, the taking-out work becomes easy by pulling out the core member while twisting and compressing the core member. Taking in and out of the core member is especially difficult in a case where the intermediate portion 3C of the container body has a small diameter in a narrow manner. However, if the core member can be compressed by being twisted, the taking in and out becomes easy.

Although not illustrated by figures, the core member can be easily inserted into the container body by inserting the core member gripped with one hand into the container body and rotating the container body side, in inserting the core member into the container body. That is, at a stage where the front end section of the core member reaches the small-diameter portion 3C of the container body, the core member is caught on and cannot move forward from there. However, at this stage, by twisting the core member in the direction illustrated in FIGS. 5A and 5B by rotating the container body, the dimension of the entire core member in the radius direction can be compressed. Therefore, the core member can be easily inserted through the opening 4.

That is, the core member may be twisted by a hand of a user, or may be twisted by rotating the container body side.

The second ribs (air resistance members) 50 intersect with the first ribs 40 to form a net (plurality of non-closed air cells S), and have the protruding length from the outer peripheral surface of the core main body 31 (the dimension in the outer diameter direction) that is shorter than the protruding length of the first ribs 40, and thus are not completely in contact with the inner surface of the container body even if the first ribs come in contact with the inner surface of the container body due to the expansion of the core main body. If an outer peripheral end edge of the second rib 50 comes in partially contact with (or come close to) the inner wall of the container body (or comes in entirely contact with the inner wall of the container body with light force), the contact of the second rib 50 is configured not to significantly impede circulation of the air among the plurality of non-closed air cells (non-sealed spaces) S existing in the same flow path F.

That is, the protruding length, the thickness, and the shape of the second ribs 50 are configured such that free movement of the air in the individual flow path F is impeded by the second rib 50 to temporarily increase the pressure in the individual non-closed air cell S at the time of expansion of the core main body 31, but the movement of the air between the empty spaces existing in the same flow path is still possible.

In other words, the distance between the second rib 50 and the inner surface of the container body becomes narrow or the second rib 50 and the inner surface of the container body are slightly in contact at the time of expansion of the core main body due to insertion of the penis, the second rib becomes a slight obstacle against the movement of the air among the plurality of non-closed air cells in the same path, and temporarily increase an inner pressure of the individual non-closed air cells S. However, the air in the non-closed air cells S in the same flow path F can move to another adjacent non-closed air cell S across the second rib due to increase/decrease or change of the inner pressure of the individual non-closed air cells associated with reciprocating motion of the penis in the insertion empty space 35. Further, the front end sections of the individual flow paths F in the longitudinal direction communicate with one another, and thus the follow of the air in the axial direction (including the inclined direction and the spiral direction) in the container body is secured. Especially, in the state where the small hole 3b of the container body is opened, the air coming out of the front end section of the flow path is discharged outside the container, and decreases the inner pressure between the core member and the inner wall of the container body.

When the penis is inserted in the state where the small hole 3b of the container body is blocked, an air flow toward the front end occurs in each flow path. However, the air coming out of (trying to come out of) the front end section of each flow path has no way out of the container and thus flows rearward in the flow path, and is filled in the flow path.

When an operation to insert the penis into the insertion empty space and press the penis into the deepest portion of the container body in the state where the small hole 3b is opened, and put the penis rearward, is performed, the air sucked through the small hole 3b flows rearward into the space between the adjacent first ribs (the space serving as the flow path F) and is filled therein. Meanwhile, an operation to put the inserted penis rearward in the state where the small hole 3b is closed is performed, the space between the core member and the inner wall of the container body is an airtight space, and thus the front end section of the insertion empty space where the penis has existed until then is evacuated (contracted), and the inner surface of the accommodation empty space is stuck to the outer surface of the penis.

Next, the container body 3 has a gourd-like shape where the outer diameter of the intermediate portion (small-diameter portion) 3C is smaller than the outer diameter of both end sections in the longitudinal direction, and thus the pressure applied from the container body to the front end section of the penis through the core main body is strong when the front end section of the penis passes through the insertion empty space that is narrow corresponding to the intermediate portion 3C. The second rib 50 functions as a means to reduce the strong pressurizing force (safety valve). Note that the position of the small-diameter portion 3C is not necessarily a central portion of the container body in the longitudinal direction, and may be a position deviating reward or frontward from the central portion in the longitudinal direction.

This container body 3 has the small-diameter portion 3C, and thus has a small diameter by the intermediate portion of the core member corresponding to the small-diameter portion 3C.

The outer end edge of the first rib 40 does not necessarily adhere to the inner wall of the container body in the state where the penis is not inserted in the insertion empty space 35, and it is enough to configure the outer end edge of the first rib to adhere to the inner wall of the container body and form the flow path F in conjunction with the expansion of the core main body due to insertion. At this time, the plurality of non-closed air cells S is formed among the outer surface of the core main body, the ribs 40 and 50, and the inner wall of the container body.

(Procedure of Forming Flow Path and Non-Closed Air Cell)

Next, a procedure of forming a flow path and a non-closed air cell will be described based on FIGS. 6A to 6E-2.

FIG. 6A is a front view of the core member (ejaculation promotion apparatus), FIGS. 6B-1 and 6B-2 are an A-A' cross-sectional view and a B-B' cross-sectional view illustrating a state in which an insertion object is not inserted in an insertion empty space, FIGS. 6C-1 and 6C-2 are an A-A' cross-sectional view and a B-B' cross-sectional view illustrating a state in which the insertion object is inserted into an intermediate portion in the insertion empty space, FIGS. 6D-1 and 6D-2 are an A-A' cross-sectional view and a B-B' cross-sectional view illustrating a state in which the insertion object is inserted in a deep portion of the insertion empty space, and FIGS. 6E-1 and 6E-2 are an A-A' cross-sectional view and a B-B' cross-sectional view illustrating a state in which the insertion object is inserted in a deepest portion of the insertion empty space.

FIGS. 6B-1 and 6B-2 illustrate a state where the insertion object is not inserted in the insertion empty space, and the outer end edge (outer peripheral edge) of the first rib 40 is separated from or is slightly in contact with the inner wall of the container body, as illustrated in FIG. 6B-2. At this time, neither flow path F and nor non-closed air cell S are formed.

Next, when the insertion object P is inserted through the insertion inlet 33 and the front end section of the insertion object P reaches the position B-B' that is the cross-section position, as illustrated in FIGS. 6C-1 and 6C-2, the insertion empty space 35 of the core main body is expanded by the insertion object and expands in diameter. However, the outer peripheral surface of the core main body less expands, and thus the positions of the outer end edges (outer peripheral edges) of the first ribs 40 have not substantial change, and neither the flow path F nor the non-closed air cell S are formed. Note that, this is a mere example, and the flow path and the non-closed air cell may be formed in the position B-B' at this point of time.

Next, when the front end section of the insertion object P goes beyond the cross sectional position B-B', and the outer peripheral surface (large-diameter portion) of a main body of the insertion object reaches the cross-sectional position B-B', as illustrated in FIGS. 6D-1 and 6D-2, the core main body expands as a whole, and thus portions of all of the first ribs 40 existing in positions corresponding to the position B-B' come in contact with the inner wall of the container body with pressure and adhere to the inner wall of the container body. Therefore, the flow path F is formed in a portion corresponding to the position B-B'. Further, the outer end edges (outer peripheral edges) of the second ribs (air resistance members) 50 positioned around the position B-B' are displaced in an outer diameter direction, and come close to or slightly in contact with the inner wall or the container body. Therefore, the non-closed air cells S are formed around the position B-B'.

Next, in a state where the insertion object P reaches the deepest portion, as illustrated in FIGS. 6E-1 and 6E-2, the core member expands in diameter to the maximum, and the non-closed air cells S are formed in the flow paths F corresponding to the periphery of the position B-B'. In reality, at this point of time, the flow paths and the non-closed air cells are formed not only in the periphery of the position B-B' but also in the outer diameter direction along the entire length of the insertion object P in the axial direction.

Note that, as illustrated in FIGS. 6E-1 and 6E-2, even if the front end section of the core member is in contact with an inner wall of the front end of the container body, the front end sections of all of the flow paths F are in communication with the small hole 3*b*. Therefore, the air flow flowing through all of the flow paths toward the front end is discharged outside through the small hole 3*b* in the open state as the core member expands due to insertion of the penis. That is, the front end section of the first rib (a front end opening of the flow path) is designed to communicate with the small hole 3*b* when the core member is accommodated in the container body.

Note that, in the illustrated example, the outer end edges of the second ribs 50 are separated from the inner wall of the container body at the stages of FIGS. 6D-1 and 6D-2. However, the outer end edges of the second ribs may be configured to easily retreat and be easily deformed at the time of an increase in the inner pressure of the non-closed air cells by being slightly in contact with the inner wall of the container body, and remove the air. In this case, elastic deformation may just be made easy such as thinning of the second ribs.

Note that, in the above description, deformation patterns of the ribs only in the cross-sectional position B-B' have been illustrated and described for convenience. However, the ribs exhibit similar deformation patterns according to progress and the back and forth motion of the insertion object in positions in the axial direction other than the cross-sectional position B-B', thereby to form and cancel the flow paths F and the non-closed air cells S.

Next, an operation in a state where the small hole 3*b* is opened and an operation in a state where the small hole 3*b* is closed will be described.

First, a user who grips the container body inserts the penis through the insertion inlet 33 of the core member 30 set in the container body 3 into the insertion empty space 35 in the state where the small hole 3*b* is opened, the core member is sequentially expanded and expands in diameter in the outer diameter direction from the rear end side to the front end side (FIGS. 6C-1 to 6C-2 and FIGS. 6E-1 and 6E-2). Therefore, the non-closed air cells S are sequentially formed from the rear end side to the front end side of the core member. That is, in the process where the front end section of the penis moves from the rear end side to the front end side, the air in the non-closed air cell S at the rear end side flows toward the front end side by a pressure of the penis and is sequentially moved to the adjacent non-closed air cell S, and is finally discharged through a narrow open portion of the front end section of the flow path F and discharged through the opened small hole 3*b* to an outside of the container body. Note that the air in the non-closed air cells does not completely come out by the pressure from the penis, and the air pressure in the non-closed air cells can be properly maintained according to air resistance force held by the second ribs. Therefore, an air cushion function (pressurizing force to the penis) can be maintained.

Following that, when an operation to put the penis back to the rear end side (opposite order to FIGS. 6(*a*-1) to 6(*e*-1)) is performed, the penis moves to the rear end side in the insertion empty space 35, and thus the core member is decreased in the outer diameter. Therefore, the first ribs 40 are separated from the inner wall of the container body inner wall, and the outside air is introduced through the small hole 3*b* into the container body. At this time, the flow paths F formed between the first ribs and the inner wall of the container body are cancelled, and the outside air flows into the rear end side along the first ribs.

In the state where the small hole 3*b* is opened as described above, original flexibility of the core member can be maintained, and thus a smooth operation in the insertion empty space (relative movement of the penis with respect to the core main body) becomes possible, and an adequate stimulus can be provided to the penis by the air cushion function exhibited by the non-closed air cell S.

Next, the penis is inserted into the insertion empty space in the state where the small hole 3*b* is opened, and then the small hole 3*b* is closed and the penis moves back and forth in the insertion empty space, the portions that configure the core member 30 made of a gel-like resin exhibit the elasticity, and the function as air cushion (the tightening force in an inner diameter direction) is further added due to existence of the non-closed air cells S formed at the stages of FIGS. 6C-1 and 6C-2 to FIGS. 6D-1 and 6D-2. However, the non-closed air cells are not sealed, or are merely closed in an openable state with small elastic force of the second ribs. Therefore, the second ribs function as a safety valve and prevents the pressure in the empty space from exceeding a predetermined value and being increased. This predetermined value is determined according to the protruding length of the second ribs (the interval between the second ribs and the inner surface of the container body) and elastic deformability (the thickness, shape, and hardness).

That is, when the penis is pushed into the front end side in the state where the small hole 3*b* is closed, the first ribs 40 adhere to the inner surface of the container body, whereby to form the non-closed air cells S with the outer peripheral surface of the core main body and the second ribs 50. While the non-closed air cell S exhibits the function as air cushion and generates adequate pressurizing force to the penis, the inside air flows into the adjacent non-closed air cell S side through a gap between the second rib 50 and the inner wall of the container body if the inner pressure is tried to increase by more than a predetermined value. Therefore, the inner pressure of the non-closed air cells is prevented from being excessive, and the pressurizing force to the penis can be prevented from being excessive.

If the user feels the tightening force due to the air cushion by the non-closed air cells is excessive, fine adjustment to properly decrease the inner pressure of the entire container body is possible by appropriate removal of an appropriate amount of air through the small hole 3b.

Note that, at the closing of the small hole, the penis is pressurized in a compression direction by the narrow portion when the penis passes through the narrow portion rearward, and thus a sticking effect by the pressurizing force can be further enhanced in addition to a sticking effect by vacuum.

(Characteristic Effects in First Embodiment)

According to the ejaculation promotion apparatus and the ejaculation promotion device having the above configuration, the following effects can be obtained.

When the core main body expands more than necessary as the air pressure in the insertion empty space rises at the time of insertion of the penis, a contact pressure between the penis and the inner wall of the core main body is decreased, and sensitivity of the penis side may be decreased. Further, a similar problem occurs when the inner diameter of the insertion empty space (container) is larger than an outer diameter of the penis. To prevent such a problem, it is effective to form a plurality of air cells with a small volume between the core main body and the container body to generate a cushion action (a pressurizing action to the penis). This is because the air cells can provide pressuring force in the inner diameter direction (expansion regulation force in the outer diameter direction) to the outer peripheral surface of the core main body. Conventionally, the defect of a decrease in the stimulus and the pressurizing force to the penis due to expansion of the core main body in the outer diameter direction more than necessary at the time of the insertion of the penis or the rubbing operation by the air cushion by elastic force of the ribs and the airtight empty space has been prevented, by causing the ribs to intersect with one another in a net-like manner, the ribs being projectingly provided from the outer peripheral surface of the core main body, and forming the airtight empty spaces between the ribs and the inner surface of the container.

However, the conventional airtight empty space that cannot remove the air unless the penis is removed from the insertion empty space generates a high pressure proportional to the pressure received from the penis in the insertion empty space, and acts in a direction of compressing the core main body. Therefore, the pressure from the core main body to the penis becomes excessive, and becomes a cause to cause a pain or deteriorate sensitivity of the penis.

In the present invention, the plurality of air resistance members (second ribs) 50 is intermittently provided along the longitudinal direction of the flow paths F formed between the plurality of first ribs 40 extending in the axial direction (including the direction inclined with respect to the axial direction). The air resistance member (second rib) 50 has a shorter protruding length (or more easily elastically deformable) than the first rib. Therefore, at the time of insertion of the penis (when the penis moves toward the front end of the core main body along the inner wall of the insertion empty space 35), the core main body expands, so that the air resistance members 50 become a resistance when the air moves toward the front end in the flow paths, while the flow paths are formed by the first ribs. Therefore, the inner pressure in the non-closed air cells formed between the two adjacent first ribs that configures the flow path and two adjacent air resistance members (second ribs) 50 provided in the flow path is temporarily increased, and functions as air cushion (pressurizing force in the inner diameter direction).

Meanwhile, the second rib 50 as the air resistance member is configured not to completely impede the movement of the air along the flow path. Therefore, when the inner pressure of the non-closed air cells S exceeds a predetermined value, the air removal is automatically performed and the inner pressure is decreased.

Therefore, the air resistance member functions as a safety valve that allows the air removal from the non-closed air cell, and the air to be stagnated in the non-closed air cell goes beyond the air resistance member by fixed pressing force or more force from the penis and moves to a downstream side. That is, the non-closed air cell is compressed by the pressure from the penis, and a part of the air that has functioned as the air cushion by being stagnated in the non-closed air cell is discharged from the non-closed air cell and moves to the next non-closed air cell at the downstream side.

When the penis is inserted and the core member expands, the interval (gap) between the air resistance member 50 and the inner wall of the container body becomes narrow, or are in contact with each other with light force. Therefore, the air pressure in the non-closed air cell S formed by two adjacent air resistance members in one flow path is temporarily increased. However, when the air pressure exceeds fixed pressure, the air goes beyond the air resistance member and moves to the downstream side, and finally flows to the front end of the container body and flows out through the small hole (air removal hole) 3b. Therefore, the pressure in the non-closed air cell cannot become excessive, and excessive pressurizing force can be prevented from acting on the penis.

As described above, the non-closed air cells having the air removal function is formed instead of not forming an airtight empty space in the flow path. Therefore, the non-closed air cells exhibit the air cushion effect at the time of expansion of the core member in the container in the outer diameter direction, and an excessive load cannot be applied to the penis from the non-closed air cells having a structure to be smoothly decompressed according to the applied pressure. Especially, the plurality of non-airtight spaces is formed between the outer surface of the core member and the inner wall of the container by the ribs included in the core member made of elastomer having a cushioning characteristic, and generation of excessive tightening to the penis is avoided using the cushion action of the non-sealed spaces. Therefore, soft feeling can be obtained during a rubbing operation.

Further, a part of the air in the non-closed air cells is leaked at every rubbing operation, and the pressure and the stimulus are changed. Since the pressure and the stimulus are changed at every insertion and removal, a variable stimulus can be provided. Further, the feeling of adhesion by the pressure and vacuum can be arbitrarily adjusted.

Further, by performing the rubbing operation using an operation to open and close the small hole provided in an appropriate place in the container with a finger together, the pressure to be applied to the penis can be adjusted even if the inner pressure in the container is increased as the small hole is closed, and the stimulus can vary.

Therefore, even if an old man or a physically handicapped person, who is more sensitive to the stimulus than a healthy person as well as a healthy young man, uses this type of collecting device, a minimum stimulus suitable for the person can be provided and the object of collection can be achieved.

The second rib may have a short-length and thin structure, and thus the use amount of the expensive gel-like resin can be decreased and the manufacturing cost can be reduced.

Note that the above effects are common in other embodiments.

Second Embodiment

FIGS. 7A to 7F are main configuration explanatory views of an ejaculation promotion apparatus according to a second embodiment of the present invention, and FIG. 7A is a front view, FIG. 7B is a top view, FIG. 7C is a bottom view, FIGS. 7D and 7E are perspective views, and FIG. 7F is an A-A' cross-sectional view. Right and left views and a rear view look nearly similar to the front view, and thus illustration is omitted. Note that the same portion as the first embodiment is denoted with the same reference sign, and description is given.

An ejaculation promotion apparatus 30 according to this embodiment is different from that of the first embodiment in a structure where a plurality of narrow belt-like first ribs 40 linearly extends nearly in parallel to an axial direction on an outer peripheral surface of a core main body.

The first ribs 40 may have any form as long as the first ribs 40 can form flow paths F extending in a longitudinal direction between the first ribs by extending along a core main body 31 along the longitudinal direction at the time of expansion of the core main body.

Second ribs (air resistance members) 50 serving as a resistance against an air flow are provided in the individual flow paths F, so that an air pressure in non-closed air cells can be appropriately adjusted by an air removal action of the second ribs when the non-closed air cells S are formed, which is similar to the first embodiment.

In the present example, a core member 30 is provided with a small-diameter portion in an intermediate portion in the longitudinal direction, in accordance with the shape of a container body 3 having a small-diameter portion (narrow portion) 3C. However, in a case where the container body has a straight shape (a waistless shape), the core member also has an approximately waistless shape.

Next, FIGS. 8A to 8F are main configuration explanatory views of an ejaculation promotion apparatus according to a deformation example of the second embodiment of the present invention. FIG. 8A is a front view, FIG. 8B is a top view, FIG. 8C is a bottom view, FIGS. 8D and 8E are perspective views, and FIG. 8F is an A-A' cross-sectional view. Right and left views and a rear view look nearly similar to the front view, and thus illustration is omitted. Note that the same portion as the first embodiment is denoted with the same reference sign, and description is given.

A different point of an ejaculation promotion apparatus according to this embodiment from the ejaculation promotion apparatus of FIGS. 7A to 7F is that the entire shape excluding a front end section and a rear end section is an approximately waistless shape.

An ejaculation promotion apparatus 30 according to this embodiment is the same as the embodiment of FIGS. 7A to 7F in a configuration in which first ribs 40 linearly extend nearly in parallel to an axial direction, but is different in that a small-diameter portion (narrow portion) does not exist in a central portion in the axial direction. As a container used for this ejaculation promotion apparatus, a waistless type without having a narrow portion in a central portion in a longitudinal direction is suitable.

There are no different points from the embodiment of FIGS. 7A to 7F except for the above-described configurations.

Therefore, when the core main body 31 expands by more than a predetermined amount, flow paths F are formed between the first ribs 40, and non-closed air cells S are formed between second ribs 50 in the flow paths.

When the core main body 31 expands by more than a predetermined amount due to insertion of a penis, an inner pressure is increased, and thus the non-closed air cells S generate pressurizing force to the penis by an air cushion action. Meanwhile, when the inner pressure in the non-closed air cells exceeds a predetermined value, the second ribs function as an air removal valve, by making the length short or with other creative means.

Therefore, an excessive load can be prevented from being applied to the penis.

Third Embodiment

Figure 9A:
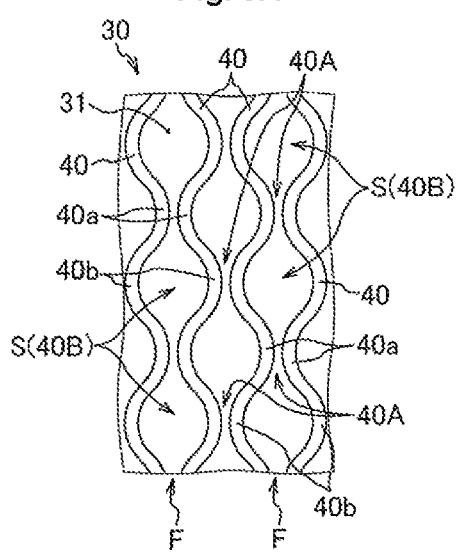
FIGS. 9A and 9B are main configuration explanatory views of an ejaculation promotion apparatus according to a third embodiment of the present invention.
Figure 9B:
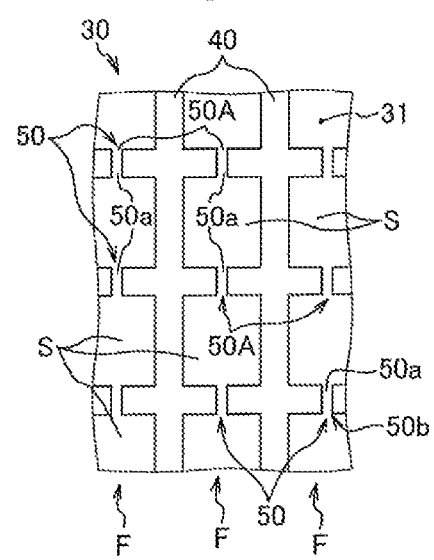

FIGS. 9A and 9B are main configuration explanatory views (front enlarged main portion cross-sectional view) of an ejaculation promotion apparatus 30 according to a third embodiment of the present invention.

In the embodiment of FIG. 9A, flow paths F and non-closed air cells S are formed only with first ribs 40.

That is, in the embodiment of FIG. 9A, the first ribs 40 are formed in a waveform manner (or in a zigzag manner), and two adjacent first ribs are configured to be line symmetry.

Therefore, at the time of expansion of the core main body, an air removal gap 40A is formed between approach portions (air resistance members) 40a of two adjacent first ribs, and a space 40B serving as a non-closed air cell S is formed between two adjacent separated portions 40b.

The gaps 40A can discharge the air in the non-closed air cells S formed in the spaces 40B along the flow paths F when the core main body 31 expands.

Air removal property may be secured by making the thickness of the approach portion 40a thinner than the separated portion 40b to enable easy elastic deformation, or by making a protruding length of the approach portion 40a (a protruding length from a peripheral surface of the core main body) shorter than a protruding length of the separated portion 40b.

Next, in the embodiment of FIG. 9B, a second rib (air resistance member) 50 is provided (protrudes) across facing inner walls of first ribs 40 that are parallel to the axial direction of a core member 30 and linearly extend, and a through-hole 50a is formed in an appropriate place in the second rib 50, so that this through-hole 50a forms an air removal and ventilation gap 50A at the time of expansion of the core member. In this example, the first rib and the second rib have equivalent protruding lengths. However, by making the second protruding length short, an air removal property may be enhanced, and the use amount of the gel may be decreased.

In this embodiment, non-closed air cells S are formed between adjacent second ribs 50.

According to this configuration, the air in the non-closed air cells S formed between the second ribs 50 can be discharged through the gaps 50A when the core main body 31 expands.

<Summary of Configurations, Actions, and Effects of Present Invention>

The ejaculation promotion apparatus 30 according to the first present invention is an ejaculation promotion apparatus made of a gel-like resin accommodated in the container body 3 with at least the one end surface in the axial direction open, and including the insertion empty space 35 extending through the insertion inlet 33 in the one end surface in the axial direction into the inside, and the ejaculation promotion apparatus including the core main body 31 including the insertion inlet and the insertion empty space, and the plurality of first ribs 40 projectingly provided on the outer peripheral surface of the core main body at necessary intervals and extending in approximately parallel to one another, wherein each of the first ribs comes in contact with the inner wall of the container body and form a flow path F extending in the axial direction or in the direction inclined with respect to the axial direction with the adjacent first rib at least at the time of expansion of the core main body, and an air resistance member 50 (convex portion 40a) that allows passage of air along the flow path while serving as a resistance against movement of the air at the time of expansion of the outer diameter of the core main body is provided in the flow path.

Further, in the ejaculation promotion apparatus 30 according to the second present invention, the air resistance members 50 are the plurality of second ribs 50 projectingly provided on the outer peripheral surface of the core main body at necessary intervals, and intersecting with the first ribs.

The air resistance member (the second rib 50 as an example thereof) is a means to impede the flow of the air in the flow path F, but is not a means to fully block the flow of the air. The air resistance member is configured not to form a sealed space in cooperation with the first rib on a steady basis when coming in contact with the inner wall of the container body, by enabling easy elastic deformation by making the protruding length of the air resistance member shorter than that of the first rib, or by making the air resistance member thinner than the first rib even if the protruding length is the same. Alternatively, the air resistance member (second rib) is configured such that the space (non-closed air cell) is immediately opened due to an increase in the internal pressure even if the sealed space is temporarily formed.

The first ribs and the second ribs may be configured to intersect in a net-like manner. However, the arrangement of the ribs may not be the net-like arrangement as long as the second ribs that bring the air resistance in the flow path are provided.

According to the present invention, the non-closed air cells serving as the air cushion are formed between the outer peripheral surface of the core main body and the inner wall of the container body due to the existence of the ribs. Therefore, an excessive stimulus during an operation for penis rubbing is prevented, compared with a case where the sealed space is formed, and even if an old man or a physically handicapped person who are more sensitive to the stimulus than a healthy person as well as a healthy young man uses this type of collecting device, a stimulus that is suitable for the person and is also necessary and sufficient can be provided and the object of ejaculation (sperm sampling) can be achieved.

The air in the plurality of non-closed air cells forms a cushioning portion (air cushion portion), an elastic portion, or a repulsive portion, and produces a tightening pressure to the penis. Further, when the tightening pressure becomes excessive, the air flows out through the gap between the second rib and the container body, and thus a decrease in operability, occurrence of uncomfortable feeling, a decrease in the sensitivity of the user, and the like due to the excessive tightening pressure can be prevented.

Further, in a case where the sealed space serving as the air cushion is formed between the outer peripheral surface of the core member and the inner wall of the container body, there is a concern that, when an old man, a physically handicapped person, or the like, who is more sensitive to the stimulus than a healthy young man, uses this type of collecting device, a strong stimulus not suitable for the person is provided and the objectives of ejaculation promotion and sperm sampling cannot be achieved, due to the excessive air pressure force applied to the penis.

In the present invention, the plurality of second ribs 50 provided along the flow path F is configured to serve as resistances against the air moving in the flow path, and the second ribs are configured not to completely hinder the movement of the air. That is, the spaces formed between the first and second ribs and the inner surface of the container body at the time of expansion of the core member are caused to be the non-closed air cells (incomplete sealed spaces), so that excessive pressurizing force does not act on the penis in the core member.

That is, in using the ejaculation promotion device, a cap 5 is removed, and the penis is inserted through the insertion inlet 33. The core main body expands due to the insertion, and the outer end edges of the first ribs 40 adhere to the inner wall of the container body (are in contact with the inner wall of the container body with a pressure). Therefore, the plurality of flow paths F is formed between the first ribs 40 and the outer peripheral surface of the core main body outer peripheral surface. These flow paths F are uniformly formed throughout the entire outer peripheral surface of the core main body, and thus can exhibit the function as the air cushion to the entire outer surface. Further, the air pressure that generates the air cushion is not constant and is increased/decreased because the air goes beyond the second ribs and flows due to the pressure from the penis. Therefore, the excessive pressurizing force can be prevented from being applied to the penis. The elastic force and tightening bring the feeding of adhesion.

Since the gel-like resin that configures the core member is expensive, a decrease in the use amount of the gel-like resin is required to achieve price reduction of product pricing. According to the present invention, the use amount of the materials that configures the second rib can be considerably decreased compared with the first rib, and thus there is a cost reduction effect. The air cushion effect equivalent to that of the sperm collection device of Patent Document 1 is exhibited, and the problem of excessive pressurizing to the penis, which is a drawback of Patent Document 1, can be solved, and a decrease in the use amount of the gel-like resin is achieved. The second rib also plays a role of reinforcing the first rib.

Further, the use material of the air resistance member is decreased compared with that of the first rib. Therefore, the volume of the entire core member is decreased, and the work of taking in and out the core member to/of the container becomes easy. Therefore, repetition of washing the core member after use, attaching the core member into the container again, and re-using the device becomes possible and it is cost efficient.

The shape of the core member may be devised while using the container having a simple shape, whereby the pressure applied to the penis inside can be adjusted, and the stimulus can be changed.

In the ejaculation promotion apparatus 30 according to a third present invention, each of the first ribs 40 extends in the axial direction of the core main body 31 or in the direction inclined with respect to the axial direction.

The direction inclined with respect to the axial direction means a direction other than a direction parallel to the axial direction.

The direction inclined with respect to the axial direction includes a spiral manner.

By configuring the first ribs in a spiral manner, the outer diameter can be reduced when the core member is twisted along the spiral, and thus insertion work into the container body becomes easy. After insertion, the shape returns to the original shape by restoring force of the core member. Especially, in a case where the inner diameter of the container body is small, the insertion work becomes easy with such a spiral structure.

Note that the shape of the first rib is not limited to a linear shape or a curved shape, and other various forms may be employed. For example, various forms such as a zigzag shape, a waveform, or a non-uniform shape can be expected.

In the ejaculation promotion apparatus according to a fourth present invention, the interval between the adjacent first ribs is narrowest at the end surface side opposite to the one end surface where the insertion inlet is provided.

The flow path extending in the axial direction, in the direction inclined with respect to the axial direction, or in a curved direction is formed between two adjacent first ribs. A termination section of the flow path at a guidance side in an insertion direction of the penis is made narrower than the flow path at an upstream side. Therefore, the air flow in the flow path at the termination section can be easily stagnated, and a decrease in the inner pressure in the flow path at the time of insertion of the penis is delayed, and the air pressure in the non-closed air cell can be prevented from being easily decreased (without exhibiting a sufficient air cushion effect).

In the ejaculation promotion apparatus according to a fifth present invention, the protruding length of the air resistance member from the outer peripheral surface of the core main body is shorter than the protruding length of the first rib.

By causing the protruding length of the air resistance member to be a short length, the gel-like resin that is a use material is decreased, and manufacturing cost can be reduced.

The ejaculation promotion device according to a sixth present invention includes the ejaculation promotion apparatus and the container body that accommodates the ejaculation promotion apparatus in an opening in one end surface in the axial direction.

The ejaculation promotion device according to a seventh present invention is provided with the small-diameter portion in at least a part of the outer peripheral surface of the container body.

In the case of providing the small-diameter portion, the core member is held in the container side by the pressure between the penis in the core member and the narrow portion, and thus the core member can be prevented from deviating to the opening side of the container body or from being pulled out through the opening. Further, a stronger stimulus can be received when the penis passes through the small-diameter portion than when the penis passes through a large-diameter portion. The second rib functions as a safety valve so that the stimulus does not become an excessive stimulus with the air cushion, and maintains a proper pressure.

The ejaculation promotion device according to the eighth present invention, the air removal hole 3b is provided in the container body.

In rubbing the penis in the insertion empty space 35, the operation is conducted while blocking the air removal hole (small hole) 3b provided in the container body with a finger, so that the inner pressure in the container body is increased, and adequate feeling of pressurizing and feeling of vacuum (feeling of sticking) can be obtained.

In the state where the air removal hole is opened, original flexibility of the gel-like resin that configures the core member, and the stimulus using elasticity can be obtained. That is, in the state where the air removal hole is opened, the air between the core member and the container goes outside the container, and thus the core member is pushed by the penis and the core member is only enlarged/contracted. Meanwhile, in the state where the air removal hole is blocked, the inner pressure in the container can be made constant, and thus the feeding of vacuum that allows the core member to stick to the penis can be obtained, and the objective of ejaculation promotion can be easily achieved.

That is, by opening and closing the air removal hole, the pressure in the container can be adjusted. Therefore, at the time of insertion of the penis, feeling at the time of rubbing can be different, and the ejaculation can be promoted.

In more details, the penis is inserted into the core member in the state where the air removal hole is opened, and the core main body sequentially expands toward the front end as the insertion goes on, and thus the first ribs 40 gradually come in contact with the inner wall of the container from the rear portion side toward the front end side. In this process, the second ribs 50 also come close to the inner wall of the container inner wall. The flow of the air in the flow path F goes to the front portion by the expansion of the core main body. However, the air is stagnated by the second ribs, and the air pressure in the non-closed air cell S formed between the second ribs is increased. However, the pressure in the non-closed air cell is smoothly increased/decreased according to variation of the pressure from the penis. That is, when the pressure from the penis is increased, the air in the non-closed air cell gradually comes out, and moves along the flow path.

When the penis is pushed into the insertion empty space in the state where the air removal hole 3b is opened, the depressed air comes out through the air removal hole to an outside of the container, and thus the elasticity of the core member can be used, compared with the case where the air removal hole is closed. Further, the air cushion effect is exhibited using not only the elasticity of the core member but also the air pressure in the non-closed air cells, and the pressure can be increased without stimulating the penis in an excessive manner. That is, the non-closed air cells are gradually formed in the axial direction in the process where the penis goes to the front portion of the core member, and extra air is discharged outside the container while a cushioning characteristic using compression of the air is generated. Note that the non-closed air cells are sequentially formed from the front in the moving direction of the penis, but are sequentially crushed and the air coming out of the non-closed air cell forms an air cell at the downstream side.

In a case where the air cell is a sealed space, the air cushion obtained from the sealed space brings feeling of hard contact obtained from a balloon or a ball filled with air, and the objective of ejaculation promotion can be less easily achieved.

<Medical Study Examples Present Applicant Involved>

Medical study examples currently conducted by the present applicant in cooperation with medical research institutes such as universities and hospitals as of October 2014 are as follows:

1. A sperm sampling experiment is conducted using an ejaculation promotion device that is a product of the present applicant in the urology department, Dokkyo Medical University Koshigaya Hospital.

This is experiment and study as to which of a case of using the ejaculation promotion device and a case of an ejaculation conduct with a hand can collect more favorably sperms.

The sperms collected using the ejaculation promotion device TENGA (registered trademark, deep throat cup) that is a product of the present applicant, and the sperm ejaculated using a hand in a normal way are compared and studied. The number of subjects is 20.

Not only the quality and the amount of the sperms, but also the degrees of early cleavage are compared where the human sperms are fertilized to eggs of mouse.

The study is planned to finish at the end of October 2014. Good results have been obtained so far in the interim report.

2. Premature ejaculation rehabilitation study by Mr. Rodriguez (clinical psychotherapist, sexologist) of Spanish Sexual Function Clinic http://www.isemu.es/index.html Ejaculation has been conducted by patients with premature ejaculation, using the ejaculation promotion device that is a product of the present applicant, and improvement has been shown. Therefore, an experiment has been conducted for 20 subjects for six weeks using FLIP HOLE (registered trademark), which is a full-fledged ejaculation promotion device.

The result is to be submitted as a paper to International Journal of Sexology.

3. Premature ejaculation rehabilitation study by Professor Lim of Gleneagles Hospital in Singapore (currently in progress)

http://gleneagles.com.sg/DoctorsCV/Urology/Dr-Lim-Huat-Chye-Peter?speciality=UROLOGY Effects between a case of rehabilitation treatment using the ejaculation promotion device (registered trademark, TENGA) and a case of using a treatment drug are compared and studies for people who have gotten the highest point in premature ejaculation.

The term of the experiment is three months, and the experiment is in progress as of October 2014.

DESCRIPTION OF THE REFERENCE NUMERALS

1 . . . ejaculation promotion device, 2 . . . container, 3 . . . container body, 3A, 3B . . . large-diameter portion, 3C . . . small-diameter portion, 3a . . . other end section, 3b . . . small hole (air removal hole), 4 . . . opening, 10 . . . locking member, 10a . . . convex portion, 30 . . . core member (ejaculation promotion apparatus), 31 . . . core main body, 33 . . . insertion inlet, 35 . . . insertion empty space, 37 . . . flange, 37a . . . first flange, 37b . . . second flange, 37c . . . concave portion, 39 . . . folds or the like, 40 . . . first rib, 40a . . . approach portion (air resistance member), 40b . . . separated portion, 40A . . . air removal gap (air resistance member), 40B . . . space, 50 . . . second rib (air resistance member), 50a . . . through-hole, 50A . . . gap, F . . . flow path, S . . . non-closed air cell

The invention claimed is:

1. An ejaculation promotion apparatus made of elastomer, accommodated in a container body with at least one end surface in an axial direction open and including an insertion empty space extending from an insertion inlet in the one end surface in the axial direction into an inside, the ejaculation promotion apparatus comprising:
    a core main body including the insertion inlet and the insertion empty space; and
    a plurality of first ribs projectingly provided on an outer peripheral surface of the core main body at intervals and extending in approximately parallel to one another, wherein
    each of the first ribs comes in contact with an inner wall of the container body to form a flow path extending in the axial direction or a direction inclined with respect to the axial direction with an adjacent first rib of the first ribs at least at a time of expansion of the core main body,
    an air resistance member that allows passage of air along the flow path while being a resistance against movement of the air in the flow path at a time of expansion of an outer diameter of the core main body,
    the air resistance member comprises a plurality of second ribs projectingly provided on the outer peripheral surface of the core main body at intervals, and intersecting with the first ribs, and
    a protruding length of the air resistance member from the outer peripheral surface of the core main body is shorter than a protruding length of the first ribs.

2. The ejaculation promotion apparatus according to claim 1, wherein each of the first ribs extends in an axial direction of the core main body, or a direction inclined with respect to the axial direction.

3. The ejaculation promotion apparatus according to claim 1, wherein the intervals between the adjacent first ribs are narrowest at an end surface side opposite to the one end surface where the insertion inlet is provided.

4. An ejaculation promotion device comprising:
    the ejaculation promotion apparatus according to claim 1; and
    a container body accommodating the ejaculation promotion apparatus in an opening in one end surface in an axial direction.

5. The ejaculation promotion device according to claim 4, wherein a small-diameter portion having an outer diameter which is smaller than outer diameters of both end sections in the longitudinal direction of the container body is provided in at least a part of an outer peripheral surface of the container body.

6. The ejaculation promotion device according to claim 4, wherein an air removal hole is provided in the container body.

* * * * *